United States Patent [19]

Lunn

[11] 4,401,668
[45] Aug. 30, 1983

[54] PYRAZINIUM SUBSTITUTED CEPHALOSPORINS

[75] Inventor: William H. W. Lunn, Indianapolis, Ind.

[73] Assignee: Eli Lilly and Company, Indianapolis, Ind.

[21] Appl. No.: 307,984

[22] Filed: Oct. 2, 1981

[51] Int. Cl.³ .................. A61K 31/545; C07D 501/46
[52] U.S. Cl. ....................................... 424/246; 544/22
[58] Field of Search .......................... 544/22; 424/246

[56] References Cited

U.S. PATENT DOCUMENTS

| 4,024,133 | 5/1977 | Cook et al. | 544/30 |
| 4,200,575 | 4/1980 | Numata et al. | 424/246 |
| 4,258,041 | 3/1981 | O'Callaghan et al. | 424/246 |
| 4,278,671 | 7/1981 | Ochiai et al. | 424/246 |

FOREIGN PATENT DOCUMENTS 2043641 11/1980 United Kingdom .

OTHER PUBLICATIONS

Derwent Abstract 32890.

Primary Examiner—Paul M. Coughlan, Jr.
Attorney, Agent, or Firm—William B. Scanlon; Arthur R. Whale

[57] ABSTRACT

Cephalosporin broad spectrum antibiotics represented by the formula

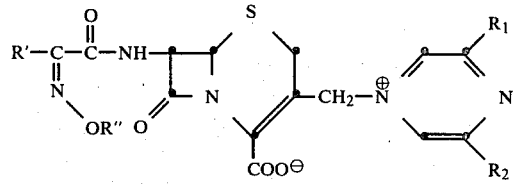

wherein R' is an amino-substituted 5- or 6-membered nitrogen heterocyclic ring, eg. 2-aminothiazol-4-yl and 3-aminopyridin-1-yl; R" is hydrogen, $C_1$–$C_4$ alkyl, a carboxy-substituted alkyl or cycloalkyl group, or a carbamoyl or substituted carbamoyl group; and $R_1$ and $R_2$ are hydrogen, $C_1$–$C_4$ alkyl, mono or di($C_1$–$C_4$ alkyl)amino, mono or di(hydroxy-substituted $C_2$–$C_4$ alkyl)amino; are provided. These betaine cephalosporins are provided in antibiotic formulations and are useful in a method for treating infections.

19 Claims, No Drawings

PYRAZINIUM SUBSTITUTED CEPHALOSPORINS

BACKGROUND OF THE INVENTION

This invention relates to cephalosporin antibiotic compounds. In particular, it relates to cephalosporin antibiotics substituted in the 3-position with a pyrazinium or substituted pyrazinium group, and in the 7-position with a 2-(5- or 6-membered heterocyclic)-2-oximinoacetyl side chain.

A number of semi-synthetic cephalosporin antibiotics substituted in the 3-position with a quaternary ammonium group have been described since cephalosporin $C_A$ (pyridine) was prepared by Hale, Newton, and Abraham, Biochem. J. 79, 403 (1961). The well-known clinical antibiotic cephaloridine, 7-(2-thienyl)acetamido-3-pyridinium-1-ylmethyl-3-cephem-4-carboxylate, U.S. Pat. No. 3,449,338 was the second cephalosporin antibiotic to achieve commercial success following the introduction of sodium cephalothin.

Recently, Heymes, et al., U.S. Pat. No. 4,152,432 describe 7-[2-(2-aminothiazol-4-yl)-2-methoxyiminoacetamido]-3-acetoxymethyl-3-cephem-4-carboxylate as a potent antibiotic. Others have described 3'-quaternary ammonium derivatives of compounds having such an aminothiazole oximino side chain with enhanced potency. For example, O'Callaghan, et al., U.S. Pat. No. 4,258,041, describe the 3-pyridinium substituted derivative, syn-7-[2-(2-aminothiazol-4-yl)-2-(2-carboxyprop-2-yl)oxyiminoacetamido]-3-(pyridinium-1-ylmethyl)-3-cephem-4-carboxylate. British patent application No. 2,043,641A describes compounds having like 7-position side chains but substituted in the 3'-position with a pyridazinium group.

SUMMARY

The cephalosporin antibiotics of this invention are substituted in the 3'-position with a pyrazinium or substituted pyrazinium group and are represented by the formula I

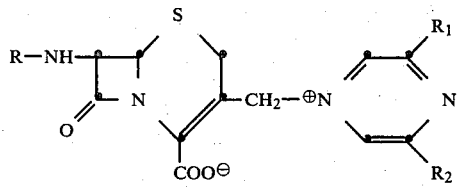

wherein R is hydrogen, formyl, or an oximino-substituted acyl group of the formula

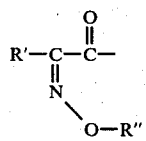

wherein R' is a 5- or 6-membered heterocyclic nitrogen-containing ring and R'' is eg. hydrogen or $C_1$–$C_4$ alkyl. The compounds are broad spectrum antibiotics, for example, 7-[2-(2-aminothiazol-4-yl)-2-methoxyiminoacetamido]-3-(pyrazinium-1-ylmethyl)-3-cephem-4-carboxylate is a potent broad spectrum antibiotic having high activity against gram-negative organisms such as pseudomonas species. Antibiotic formulations comprising a compound of the invention and a method for treating infections in man and animals are provided.

DETAILED DESCRIPTION

The cephalosporin compounds of this invention are represented by the following structural formula I

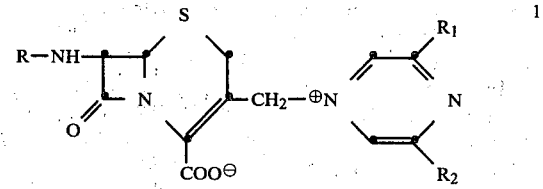

wherein R is hydrogen, formyl or an acyl group represented by the formula

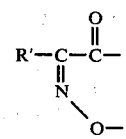

wherein R' is a 5-membered heterocyclic ring represented by the formulas

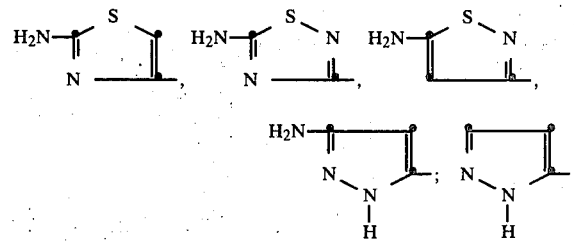

or an amino-substituted 6-membered heterocyclic ring represented by the formulas

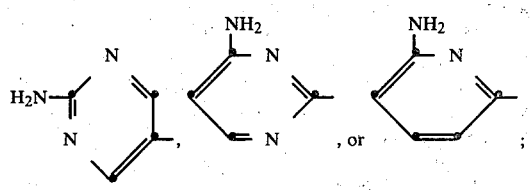

R'' is hydrogen, $C_1$–$C_4$ alkyl, or a carboxy-substituted alkyl or carboxy-substituted cycloalkyl group represented by the formula

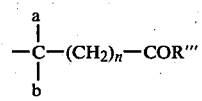

wherein a and b independently are hydrogen or $C_1$–$C_3$ alkyl, and when a and b are taken together with the carbon atom to which they are attached form a 3- to 7-membered carbocyclic ring; n is 0 to 3; and R''' is hydroxy, $C_1$–$C_4$ alkoxy, amino, or —OR° wherein R° is a carboxy-protecting group; or R'' is a substituted carbamoyl group represented by the formula

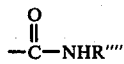

wherein R'''' is $C_1$–$C_4$ alkyl, phenyl or phenyl substituted $C_1$–$C_3$ alkyl; $R_1$ is hydrogen, $C_1$–$C_4$ alkyl, chloro, amino, $C_1$–$C_4$ alkylamino, di($C_1$–$C_4$ alkyl)amino, $C_2$–$C_4$ hydroxyalkylamino, or di($C_2$–$C_4$ hydroxyalkyl)amino; $R_2$ is hydrogen or $C_1$–$C_4$ alkyl; and the pharmaceutically acceptable, non-toxic salts thereof.

In the above definition of the compounds of the invention, "$C_1$–$C_4$ alkyl" refers to methyl, ethyl, n-propyl, isopropyl, n-butyl, t-butyl, iso-butyl, and sec-butyl; "$C_1$–$C_4$ alkoxy" refers to methoxy, ethoxy, n-propoxy, isopropoxy, sec-butoxy, and the like; "$C_1$–$C_4$ alkylamino" refers to methylamino, ethylamino, n-propylamino, n-butylamino, t-butylamino, and like mono-lower-alkylamines; "di($C_1$–$C_4$ alkyl)amino" refers to dimethylamino, diethylamino, di-n-propylamino, di-n-butylamino, methylethylamino, methyl-n-propylamino, methyl-n-butylamino, and like di-loweralkylamino groups; "$C_2$–$C_4$ hydroxyalkylamino" refers to 2-hydroxyethylamino, 1-hydroxyethylamino, 3-hydroxypropylamino, 4-hydroxybutylamino, 2-hydroxybutylamino, 2-hydroxypropylamino, and the like; and "di($C_2$–$C_4$ hydroxyalkylamino" refers to di(2-hydroxyethyl)amino, di(3-hydroxypropyl)amino, di(4-hydroxybutyl)amino, di(2-hydroxypropyl)amino, and the like.

With respect to the term R''' in formula 1, the carboxy-substituted alkyl group (R''' is hydroxy) represented by the formula

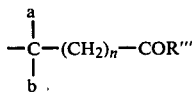

is illustrated by carboxymethyl, 2-carboxyethyl, 1-carboxyethyl, 3-carboxypropyl, 2-carboxypropyl, 4-carboxybutyl, 3-carboxypentyl, 4-carboxyheptyl, 2-carboxybutyl, and the like. When a and b are taken together, examples of the carboxy-substituted $C_3$–$C_7$ carbocyclic rings are 1-carboxycycloprop-1-yl, 1-carboxycyclobut-1-yl, 1-carboxymethylcyclobut-1-yl, 1-carboxycyclopent-1-yl, 1-carboxycyclohex-1-yl, 1-carboxycyclohep-1-yl, 1-carboxyethylcyclopent-1-yl, 1-carboxypropylcyclohex-1-yl, and the like. Examples of such groups when R''' is $C_1$–$C_4$ alkoxy are ethoxycarbonylmethyl, methoxycarbonylpropyl, 2-ethoxycarbonylprop-2-yl, t-butyloxycarbonylmethyl, 3-ethoxycarbonylpropyl, 1-ethoxycarbonylcyclobut-1-yl, 1-(methoxycarbonylmethyl)cyclopent-1-yl, and like groups. Examples of such groups when R''' is amino are aminocarbonylmethyl, 2-aminocarbonylethyl, 3-aminocarbonylpropyl, 2-aminocarbonylprop-2-yl, 1-aminocarbonylcycloprop-1-yl, 1-aminocarbonylcyclohex-1-yl, and like carboxamido substituted alkyl and cycloalkyl groups.

The compounds of the formula 1 wherein R''' is —OR° are carboxy-protected ester derivatives wherein the carboxy group (R''' is OH) is protected by a carboxy-protecting-ester group, R°, for example, an ester such as t-butyl, 2,2,2-trichloroethyl, 2-iodoethyl, benzyl, substituted benzyl eg. p-nitrobenzyl, p-methoxybenzyl, and diphenylmethyl; and trialkylsilyl esters such as trimethylsilyl. Such esters are commonly used to temporarily protect the carboxylic acid function in the cephalosporin art during the preparation of antibiotic compounds. These esters of the formula 1 wherein R''' is —OR° are intermediates useful for preparing the free acids wherein R''' is hydroxy. The ester function, R°, is removed under known conditions of hydrolysis or hydrogenolysis.

Illustrative of the N-substituted carbamoyl groups, R'', are N-methylcarbamoyl, N-ethylcarbamoyl, N-phenylcarbamoyl, N-benzylcarbamoyl, N-(2-phenylethyl)carbamoyl, and the like.

The compounds of the invention represented by formula 1 can be characterized structurally as betaines in that they possess a positively charged nitrogen atom bonded to the 3'-position of the cephem nucleus and the negatively charged carboxylate anion in the 4-position.

As is shown by the formula 1 the $R_1$ and $R_2$ groups attached to the pyrazinium moiety are in the 3- and 5-positions. Since the mono or disubstituted pyrazine used in the preparation of the compounds could apparently react at either nitrogen of the pyrazine ring, the location on the pyrazinium ring (after reaction) would depend on which nitrogen is bonded to the 3'-carbon atom. Off resonance coherent wave decoupling NMR experiments were carried out with 7-[2-(2-aminothiazol-4-yl)-2-methoxyiminoacetamido]-3-(diethylaminopyrazinium-1-ylmethyl)-3-cephem-4-carboxylate to determine which nitrogen of the pyrazine ring is the point of attachment to the cephalosporin 3'-position. The results demonstrated that the two carbon atoms of the pyrazine ring adjacent to the quaternary nitrogen, identified by $^{14}N$ coupling, were each shown to bear a hydrogen atom. Consequently, for this derivative the dimethylamino group is in the 3-position of the pyrazinium ring.

Examples of compounds of the invention include
syn-7-[2-(2-aminothiazol-4-yl)-2-methoxyiminoacetamido]-3-(pyrazinium-1-ylmethyl)-3-cephem-4-carboxylate,
syn-7-[2-(2-aminothiazol-4-yl)-2-carboxymethoxyiminoacetamido]-3-(pyrazinium-1-ylmethyl)-3-cephem-4-carboxylate,
syn-7-[2-(2-aminothiazol-4-yl)-2-(2-carboxyprop-2-yloxyimino)acetamido]-3-(pyrazinium-1-ylmethyl)-3-cephem-4-carboxylate,
syn-7-[2-(5-amino-1,2,4-thiadiazol-3-yl)-2-methoxyiminoacetamido]-3-(pyrazinium-1-ylmethyl)-3-cephem-4-carboxylate,
syn-7-[2-(5-amino-1,2,4-thiadiazol-3-yl)-2-methoxyiminoacetamido]-3-(dimethylaminopyrazinium-1-ylmethyl)-3-cephem-4-carboxylate,
syn-7-[2-(3-aminopyrazol-5-yl)-2-methoxyiminoacetamido]-3-(3-methylpyrazinium-1-ylmethyl)-3-cephem-4-carboxylate,
syn-7-[2-(2-aminopyrimidin-5-yl)-2-ethoxyiminoacetamido]-3-(3,5-dimethylpyrazinium-1-ylmethyl)-3-cephem-4-carboxylate,
syn-7-[2-(4-aminopyrimidin-2-yl)-2-(2-carboxyprop-2-yloxyimino)acetamido]-3-(pyrazinium-1-ylmethyl)-3-cephem-4-carboxylate,
syn-7-[2-(2-aminopyridin-6-yl)-2-methoxyiminoacetamido]-3-(3-aminopyrazinium-1-ylmethyl)-3-cephem-4-carboxylate,
syn-7-[2-(2-aminothiazol-4-yl)-2-hydroxyiminoacetamido]-3-(pyrazinium-1-ylmethyl)-3-cephem-4-carboxylate, syn-7-[2-(2-aminothiazol-4-yl)-2-(N-methyl-carbamoyloxyimino)acetamido]-3-(pyrazinium-1-ylmethyl)-3-cephem-4-carboxylate, syn-7-[2-(5-amino-1,2,4-thiadiazol-3-yl)-2-hydroxyiminoacetamido]-3-(3-ethylpyrazinium-1-ylmethyl)-3-cephem-4-carboxylate, syn-7-[2-(5-amino-1,2,4-thiadiazol-3-yl)-2-(N-methyl-carbamoyloxyimino)acetamido]-3-(3-diethylaminopyrazinium-1-ylmethyl)-3-cephem-4-carboxylate, syn-7-[2-(2-aminothiazol-4-yl)-2-propoxyiminoacetamido]-3-(3-ethylaminopyrazinium-1-ylmethyl)-3-cephem-4-carboxylate, syn-7-[2-(2-aminothiazol-4-yl)-2-(1-carboxycyclopent-1-yloxyimino)acetamido]-3-(pyrazinium-1-ylmethyl)-3-cephem-4-carboxylate, syn-7-[2-(5-amino-1,2,4-thiadiazol-3-yl)-2-(N-phenyl-carbamoyloxyimino)acetamido]-3-(3,5-diethyl-pyrazinium-1-ylmethyl)-3-cephem-4-carboxylate, syn-7-[2-(2-aminothiazol-4-yl)-2-methoxyiminoacetamido]-3-[3-di(2-hydroxyethyl)aminopyrazinium-1-ylmethyl]-3-cephem-4-carboxylate, syn-7-[2-(4-aminopyrimidin-2-yl)-2-methoxyiminoacetamido]-3-[3-di(2-hydroxyethyl)aminopyrazinium-1-ylmethyl]-3-cephem-4-carboxylate, syn-7-[2-(5-amino-1,2,4-thiadiazol-3-yl)-2-(1-carboxybut-1-yloxyimino)acetamido]-3-[3-di(3-hydroxypropyl)aminopyrazinium-1-ylmethyl]-3-cephem-4-carboxylate, syn-7-[2-(2-aminothiazol-4-yl)-2-methoxyiminoacetamido]-3-[3-(2-hydroxyethyl)aminopyrazinium-1-ylmethyl]-3-cephem-4-carboxylate, syn-7-[2-(2-aminothiazol-4-yl)-2-hydroxyiminoacetamido]-3-(3-diethylaminopyrazinium-1-ylmethyl)-3-cephem-4-carboxylate, syn-7-[2-(2-aminothiazol-4-yl)-2-hydroxyiminoacetamido]-3-[3-di(2-hydroxyethyl)aminopyrazinium-1-ylmethyl]-3-cephem-4-carboxylate, syn-7-[2-(pyrazol-5-yl)-2-methoxyiminoacetamido]-3-(pyrazinium-1-ylmethyl)-3-cephem-4-carboxylate, and syn-7-[2-(pyrazol-5-yl)-2-ethoxycarbonylmethoxyiminoacetamido]-3-(3-dimethylaminopyrazinium-1-ylmethyl)-3-cephem-4-carboxylate.

Aside from the betaine salt form of the compounds of the invention, acid addition salts also can be formed with the compounds of the invention. Such salts are pharmaceutically acceptable non-toxic salts which can be used in formulating suitable antibiotic formulations for administration. Salts can be formed with the mineral acids such as hydrochloric acid, hydrobromic acid, sulfuric acid, and phosphoric acid. Salts formed with strong organic acids such as the aryl and alkyl sulfonic acids, for example, toluenesulfonic acid and methanesulfonic acid also can be formed with the compounds of the formula 1 by conventional methods. The salts formed with the strong acids such as hydrochloric acid are illustrated by the following partial structural formula

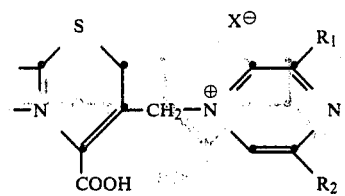

wherein $X^{\ominus}$ is the anion formed with the strong acid. A basic substituent group on the pyrazinium ring such as dialkylamino can also form salts with acids.

The compounds represented by the formula 1 can be prepared by alternative synthetic methods. In one such method a 3-halomethyl substituted cephalosporin represented by the formula 2

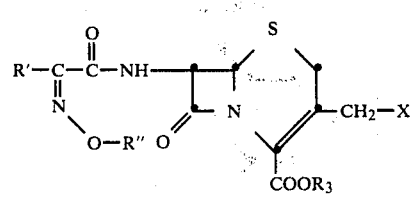

wherein R' and R'' are as defined hereinabove, X is chloro, bromo or iodo, and $R_3$ is a carboxy-protecting group; is allowed to react with pyrazine or a substituted pyrazine represented by the formula

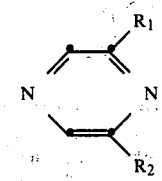

wherein $R_1$ and $R_2$ are as defined hereinabove. Preferably, X is iodo and $R_3$ is a trialkylsilyl ester carboxy-protecting group such as a tri($C_1$–$C_4$ alkyl)silyl ester, for example, trimethylsilyl or triethylsilyl.

The 3-halomethyl substituted compounds can be prepared by methods known in the art, for example, by the acylation of a 3-halomethyl-7-amino-3-cephem nucleus compound. The preferred 3-iodomethyl compounds of the formula 2 are best obtained by the method described by R. Bonjouklian, U.S. Pat. No. 4,266,049. According to this method, a 7-acylamido-3-acetoxymethyl-3-cephem-4-carboxylic acid is first silylated to block reactive groups such as the $C_4$ carboxylic acid group and the silylated derivative is reacted with a trialkylsilyliodide, eg. trimethylsilyliodide (TMSI), to form the 3-iodomethyl silylated derivative. The latter is then reacted with pyrazine or the desired substituted pyrazine and the silyl blocks are hydrolyzed to provide a compound of the formula 1. The preparation of compounds of the formula 1 by this method is illustrated by the following general reaction scheme

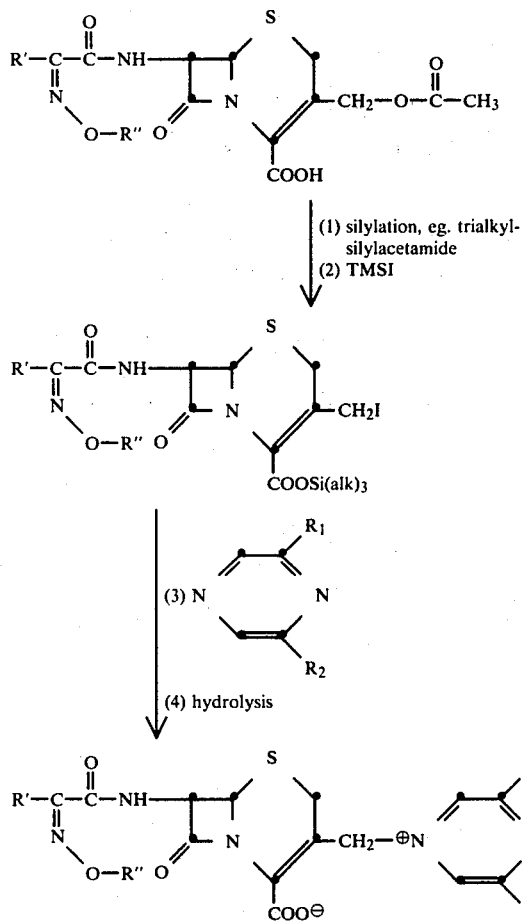

Alternatively, the compounds of the formula 1 can be prepared by the well-known displacement reaction employing a 3-acetoxymethyl-3-cephem-4-carboxylic acid. The acetoxy group is displaced by the pyrazine to form the pyrazinium compound of the formula 1 as illustrated in the following scheme.

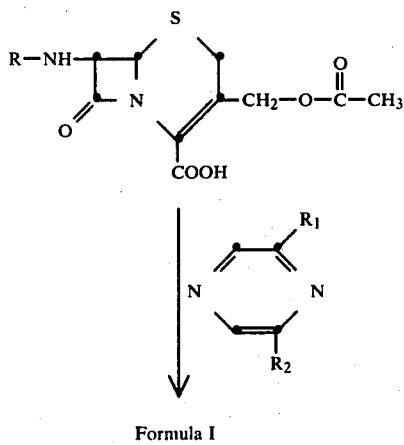

Formula I

The above reaction is carried out in an aqueous solvent comprising a water miscible organic solvent such as acetone, acetonitrile, or THF at a temperature between about 35° C. and about 65° C. In many instances the reaction yield and rate can be enhanced by the addition of a catalytic amount of an inorganic iodide such as sodium iodide.

The 7-amino-3'-pyrazinium or 3'-substituted pyrazinium compounds of the formula 1 wherein R is hydrogen also can be obtained by the N-deacylation of a 7-acylamido-3-pyrazinium (or substituted pyrazinium)-1-ylmethyl-3-cephem-4-carboxylate wherein the 7-acyl side chain is other than that in formula 1. For example, cephalosporin G, 7-phenylacetamidocephalosporanic acid, is allowed to react in the displacement reaction with pyrazine or a substituted pyrazine to provide the 3'-pyrazinium-4-carboxylate. The latter is then N-deacylated to remove the phenylacetyl side chain to obtain a 7-amino-3'-pyrazinium nucleus compound represented by the formula 3

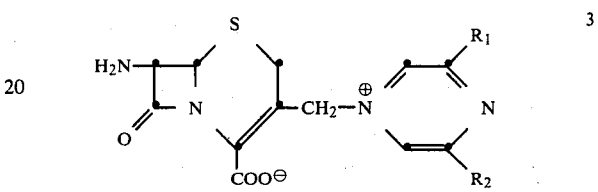

wherein $R_1$ and $R_2$ are as defined by formula 1.

The N-deacylation is carried out in an inert organic solvent, eg. a halogenated hydrocarbon solvent, by allowing the 7-acylamino compound to react with an imido halide-forming reagent such as phosphorus pentachloride. The amide linkage in the 7-position is thus converted to the imido halide which is then converted to an imino ether by the addition of an alcohol, such as methyl alcohol or isobutyl alcohol, to the reaction mixture. The imino ether is hydrolyzed to provide the nucleus compound (formula 3). The nucleus is obtained in the salt form, eg. by the hydrochloride salt form, resulting from the acid formed with the imido halide reagent in the reaction.

Examples of 7-amino nucleus compounds represented by the formula 3 are 7-amino-3-pyrazinium-1-ylmethyl-3-cephem-4-carboxylate, 7-amino-3-(3-methylpyrazinium-1-ylmethyl)-3-cephem-4-carboxylate, 7-amino-3-(3,5-dimethylpyrazinium-1-ylmethyl)-3-cephem-4-carboxylate, 7-amino-3-(3-diethylaminopyrazinium-1-ylmethyl)-3-cephem-4-carboxylate, 7-amino-3-[3-di(2-hydroxyethyl)aminopyrazinium-1-ylmethyl]-3-cephem-4-carboxylate, and the salts thereof.

In an example of the preparation of a 7-amino-3-(pyrazinium-1-ylmethyl)-3-cephem-4-carboxylate of this invention, 7-(2-thienylacetamido)cephalosporanic acid is reacted with pyrazine to form the 7-(2-thienylacetamido)-3-(pyrazinium-1-ylmethyl)-3-cephem-4-carboxylate. The latter is then converted to the trimethylsilyl ester on reaction in a halogenated hydrocarbon solvent such as methylene chloride or trichloroethane with trimethylchlorosilane in the presence of an amount of dimethylacetamide corresponding to a 4–5 molar excess. The solution of the silyl ester is cooled to a temperature of about −30° C. to about 0° C. and an imino halide-forming agent such as phosphorus pentachloride is added. The reaction mixture is stirred in the cold for from 1 to 3 hours.

The cold reaction mixture is then treated with an alcohol such as a $C_1$–$C_4$ alkanol, benzyl alcohol or, preferably, a glycol such as propylene glycol or 1,3-butanediol. The temperature of the reaction mixture is then raised to about −5° C. to about 5° C. The product precipitates, is filtered, washed with methylene chloride and dried.

During the N-deacylation any reactive substituent groups of the substituted pyrazinium group ($R_1$ and $R_2$) are protected from reaction with the imino halide-forming reagent. For example, an amino group substituent is protected. Since the 7-amino nucleus compound is used in the preparation of compounds of the invention wherein R is an acyl group via the above-described acylation, the protected substituent group is preferably left intact to likewise protect the substituent group during the subsequent N-acylation.

The compounds of the formula 1 wherein R is formyl are useful intermediates for preparing the antibiotic compounds of the invention. They can be used in a method for preparing the 7-amino-3-(pyrazinium-1-ylmethyl)-3-cephem-4-carboxylate nucleus compounds (formula 1, R=H) which is a useful alternative to the side chain N-deacylation method described above.

According to this alternative method, N-formyl 7-aminocephalosporanic acid (7-formamidocephalosporanic acid) is converted to the silylated 3-iodomethyl derivative 7-formamido-3-iodomethyl-3-cephem-4-carboxylic acid silyl ester by the method of Bonjouklian described hereinabove. The 3-iodomethyl derivative is reacted with the pyrazine to obtain a compound represented by the formula 1 wherein R is formyl. The N-formyl product is converted to the 7-amino nucleus compound (formula 1, R=H) by hydrolysis in methanolic hydrochloric acid.

The nucleus compounds represented by the formula 3 are useful intermediates for the preparation of the compounds of the formula I wherein R is an acyl group. For example, the 7-amino nucleus compound can be acylated with the oximino-substituted carboxylic acid derivative of the formula

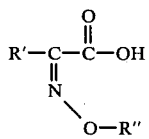

to obtain a compound of the formula 1 wherein R is acyl as defined hereinabove. The acylation is carried out with an active derivative of the carboxylic acid, eg. an active ester derivative. The active ester formed with hydroxybenzotriazole (HBT) is a preferred ester, although the ester formed with N-hydroxysuccinimide also can be used.

The 7-[2-heterocyclic-2-oximinoacetamido]-3-acetoxymethyl-3-cephem-4-carboxylic acids which are used in the preparation of the compounds of this invention are obtained by methods known in the art. For example, Heymes et al., U.S. Pat. No. 4,152,432 describe the compound wherein R' is the 2-aminothiazol-4-yl group and R'' is lower alkyl. The compounds wherein R' is the 2-aminopyridin-6-yl, 2-aminopyrimidin-5-yl, or 4-aminopyrimidin-2-yl group are prepared by the methods of U.S. Pat. No. 4,267,176. The compounds wherein R' is the 5-amino-1,2,4-thiadiazol-3-yl heterocyclic group are prepared as described by European patent application No. 0,007,470. Compounds wherein R' is the 3-aminopyrazol-5-yl or pyrazol-5-yl heterocyclic group are obtained as described by U.K. patent application No. 2,046,734A. Compounds wherein R'' is an N-substituted carbamoyl group are obtained by the procedures described by U.S. Pat. No. 4,200,575.

The compounds of the formula 1 wherein R' is a pyrazol-5-yl or 3-aminopyrazol-5-yl group are prepared by employing methods known in the art. The 2-(pyrazol-5-yl)-2-oximinoacetic acid or the 2-(3-aminopyrazol-5-yl)-2-oximinoacetic acid is prepared and converted to an active derivative of the carboxylic acid, for example, an active ester. The active ester is coupled, via N-acylation, with 7-aminocephalosporanic acid and the 7-[2-(pyrazol-5-yl)-2-oximinoacetamido]-3-acetoxymethyl-3-cephem-4-carboxylic acid and 7-[2-(3-aminopyrazol-5-yl)-2-oximinoacetamido]-3-acetoxymethyl-3-cephem-4-carboxylic acid are converted to the corresponding 3-iodomethyl silylated derivatives as described herein. The latter are reacted with the thienopyridine to provide a compound of the invention.

The pyrazole and aminopyrazole oximino substituted acetic acids are prepared by employing synthetic methods known in the art. For example, the 2-(pyrazol-5-yl)-2-alkoxyiminoacetic acid is prepared by heating in an inert hydrocarbon solvent the acetyl oximino compound of the formula A

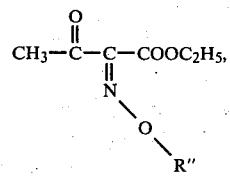

wherein R'' is other than hydrogen as defined above, with dimethylformamide dimethylacetal to form the dimethylaminomethylene oximino ester of the formula

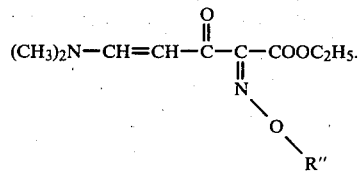

The latter is reacted with hydrazine hydrate to provide the ethyl ester of 2-(pyrazol-5-yl)-2-alkoxyiminoacetic acid. The ester is hydrolyzed to the free acid and the acid converted to an active ester for acylation.

The 2-(3-aminopyrazol-5-yl)-2-alkoxyiminoacetic acid is prepared by reacting the compound of the formula A with carbon disulfide and two equivalents of methyl iodide to form the intermediate compound of the formula B

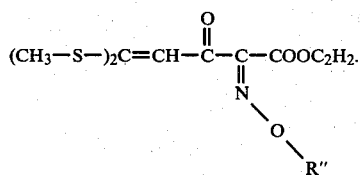

Intermediate B is reacted with N—t—BOC hydrazine to provide compound C,

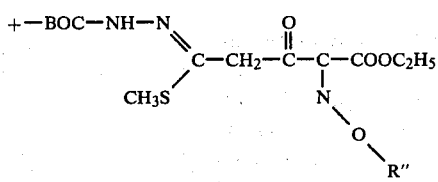

and C is reacted with hydrazine hydrate to form 2-(3-t-BOC-hydrazinopyrazol-5-yl)-2-oximinoacetic acid ethyl ester D.

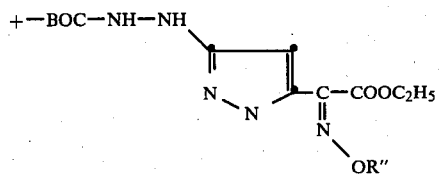

Compound D is treated in the cold with trifluoroacetic acid to remove the t-BOC group and the 3-hydrazinopyrazole is nitrosated with nitrous (HNO$_2$) acid in the cold to form 2-(3-azidopyrazol-5-yl)-2-oximinoacetic acid ethyl ester. The azido group is reduced to the amino group by chemical reduction to provide the 2-(3-aminopyrazol-5-yl)-oximinoacetic acid ethyl ester. The ester is hydrolyzed under alkaline conditions to the free acid.

The 7-acyl compounds of the formula 1 and the pharmaceutically acceptable salts thereof are potent broad spectrum antibiotics which inhibit the growth of microorganisms pathogenic to man and animals. The compounds show a high order of activity both in vitro and in vivo against gram-negative organisms such as proteus, pseudomonas, serratia, klebsiella, and salmonella. They are also highly effective in inhibiting the growth of gram-positive organisms such as staphylococcus, streptococcus and methicillin-resistant strains of staphylococci.

The compounds of the formula 1 wherein R is an acyl group and the pharmaceutically acceptable non-toxic salts thereof can be formulated into pharmaceutical compositions suitable for use in the treatment of infectious diseases. In a further aspect of this invention, there are provided antibiotic formulations comprising a compound of the formula 1 (R=acyl) or a pharmaceutically acceptable non-toxic salt thereof and a pharmaceutical diluent.

Formulations for parenteral administration of the antibiotics comprise the antibiotic or a salt thereof at a suitable concentration in a diluent such as Water-For-Injection, 5% dextrose, saline, or other pharmaceutically acceptable diluent.

The antibiotics also can be formulated in dosage unit form comprising between 100 mg and 2 g of the dry solid antibiotic in sterile vials or ampoules. The antibiotic may be in crystalline or amorphous form. Such dosage unit forms are suitable for storage and shipment of the antibiotic and, as with other cephalosporin antibiotics, the antibiotic is dissolved in the desired diluent in the vial and the solution withdrawn by syringe for injection.

In yet a further aspect of this invention, there is provided a method for the treatment and control of infections in mammals which comprises administering to the patient an effective dose of between about 100 mg and about 2 g of a compound of the formula 1 (R=acyl) or a pharmaceutically acceptable non-toxic salt thereof.

The antibiotic may be administered intramuscularly, subcutaneously or intravenously, in a single dose or in multiple doses throughout the day. When administered iv., the infusion method is most conveniently used. For example, a dosage unit formulation of the antibiotic is mixed with a physiological fluid such as 5% dextrose and administered by the drip method. Alternatively, the piggyback method of iv. infusion is conveniently used.

The particular dosage and the total number of doses administered will depend on such factors as the nature of the infection, its severity, the age and general health of the patient, as well as the tolerance of the individual patient to the antibiotic.

The compounds of the invention have the normal stereochemistry of the cephalosporin class of antibiotics. The oxime function in the side chain can be in either the syn or anti form or as a mixture of both forms. Preferred compounds of the invention are in the syn form.

A preferred group of compounds are represented by the formula 1 wherein R' is the 2-aminothiazol-4-yl heterocyclic group.

A further preferred groups are represented when R" is C$_1$-C$_4$ alkyl, with methyl being especially preferred.

Compounds of the formula 1 wherein R$_1$ is hydrogen or di(C$_1$-C$_4$ alkyl)amino and R$_2$ is hydrogen are yet another preferred group.

Especially preferred compounds of the invention are represented by the formula

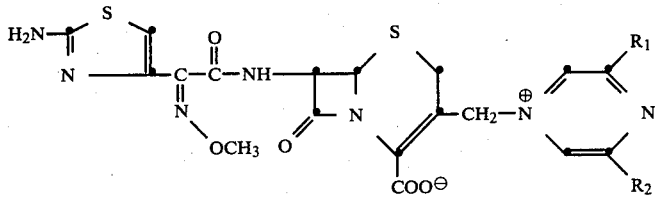

and the pharmaceutically acceptable, non-toxic salts thereof, wherein R$_1$ is hydrogen or dimethylamino and R$_2$ is hydrogen.

The following examples further illustrate the invention and the procedures by which the antibiotics are prepared.

In the examples, the abbreviations employed have the following meanings. HPLC=high performance liquid chromatography; DMSOd$_6$=deuterated dimethylsulfoxide; NMR=nuclear magnetic resonance spectrum, while the abbreviations used to characterize the signals in the spectra are: s=singlet, d=doublet, t=triplet, q=quartet, m=multiplet, b=broad, and v=very.

The NMR spectra were run on a Jeol model No. FX-90.

EXAMPLE 1 syn-7-[2-(2-Aminothiazol-4-yl)-2-methoxyiminoacetamido]-3-(pyrazinium-1-ylmethyl)-3-cephem-4-carboxylate To a suspension of 3.32 g (6.8 mmole) of syn-7-[2-(2-aminothiazol-4-yl)-2-methoxyiminoacetamido]-3-acetoxymethyl-3-cephem-4-carboxylic acid in 13.5 ml of chloroform were added 4.84 g (23.3 mmole, 4.32 ml) of N-methyl-N-trimethylsilyltrifluoroacetamide and the mixture was stirred at room temperature until a complete solution was obtained. To the solution were added 3.65 g (18.25 mmole, 2.60 ml) of trimethylsilyliodide and the mixture was stirred at room temperature for 15 minutes. The reaction mixture was evaporated to remove the chloroform and 9 ml of acetonitrile were added to form a solution of the silylated 3-iodomethyl derivative. Tetrahydrofuran (0.826 ml, 10.2 mmole) was added to the solution which was then stirred for about one hour.

A 3.5 ml aliquot of the solution of the silylated 3-iodomethyl derivative was mixed with 156.2 mg (1.95 mmole) of pyrazine and the mixture was stirred at room temperature for 2.5 hours. The reaction mixture containing the silylated title compound was chilled in an ice bath and 180 mg (10 mmole) of water were added. A tannish-brown precipitate formed, 1 ml of dry acetonitrile was added, and the precipitate was separated by filtration. The precipitate of crude product was dried and weighed 674 mg. The product was purified by HPLC. There were obtained 15 mg of purified product and 103 mg of less pure product.

NMR (DMSOd$_6$) signals at 9.7 (bs, 2H), 9.15 (bs, 2H), 6.77 (s, 1H), 5.88 (q, 1H), 5.61 (bs, 2H), 5.21 (d, 1H), 3.87 (s, 3H), and 3.53 (bs, 2H) delta.

EXAMPLE 2 syn-7-[2-(2-Aminothiazol-4-yl)-2-methoxyiminoacetamido]-3-(3-methylpyrazinium-1-ylmethyl)3-cephem-4-carboxylate A solution the trimethylsilylated derivative of syn-7-[2-(2-aminothiazol-4-yl)-2-methoxyiminoacetamido]-3-iodomethyl-3-cephem-4-carboxylic acid prepared with 2.926 g (6 mmole) of syn-7-[2-(2-aminothiazol-4-yl)-2-methoxyiminoacetamido]-3-acetoxymethyl-3-cephem-4-carboxylic acid and 3.24 g (16.2 mmole) of trimethylsilyliodide by using the silylating agent, solvents, and reaction conditions described by Example 1, was divided into four, 3.6 ml aliquots. To one, 3.6 ml aliquot were added with stirring at room temperature, 183 mg (195 mmole) of methylpyrazine. The mixture was stirred for about 30 minutes and was then treated with water. The yellow precipitate of the title compound was separated by filtration and dried. There were obtained 537 mg of the product.

NMR (D$_2$O, pH 7 buffer) signals at 9.35 (m, 1H), 9.07, 8.99 (s, d, 2H), 7.01 (s, 1H), 5.08 (d, 1H), 5.55 (q, 2H), 5.31 (d, 1H), 3.97 (s, 3H), 3.46 (q, 2H), and 2.83 (s, 3H) delta.

EXAMPLE 3 syn-7-[2-(Aminothiazol-4-yl)-2-methyloxyiminoacetamido]-3-(3,5-dimethylpyrazinium-1-ylmethyl)-3-cephem-4-carboxylate To a suspension of 4.09 g (9 mmole) of syn-7-[2-(2-aminothiazol-4-yl)-3-methoxyiminoacetamido]-3-acetoxymethyl-3-cephem-4-carboxylic acid in 18 ml of chloroform were added 5.6 ml of N-methyl-N-trimethylsilyltrifluoroacetamide and the mixture was stirred for 1.5 hours. To the resultant solution of the silylated derivative were added 3.45 ml of trimethylsilyliodide and the solution was stirred for 15 minutes. The reaction mixture was evaporated and the residue of the silylated 3-iodomethyl derivative was dissolved in 18 ml of acetonitrile and 735 μl of tetrahydrofuran were added. The solution was stirred for 5 minutes and then divided into six aliquots.

One aliquot of the solution was added to a solution of 194 mg of 2,6-dimethylpyrazine in 1 ml of acetonitrile and the mixture was stirred for 3 hours. After 145 μl of water were added to the mixture by pipette, the precipitate of crude product was separated by filtration. There were obtained 770 mg of the crude title compound which was purified by HPLC. There were obtained 210 mg of the purified product.

NMR (D$_2$O, pH 7 buffer) signals at 8.84 (s, 2H), 5.85 (d, 1H), 5.48 (q, 2H), 5.30 (d, 1H), 3.95 (s, 3H), 3.43 (q, 2H) and 2.75 (s, 6H) delta.

EXAMPLE 4 syn-7-[2-(2-Aminothiazol-4-yl)-2-methoxyiminoacetamido]-3-(3-dimethylaminopyrazinium-1-ylmethyl)-3-cephem-4-carboxylate A solution of the silylated derivative of 11.8 g of syn-7-[2-(2-aminothiazol-4-yl)-3-methoxyiminoacetamido]-3-acetoxymethyl-3-cephem-4-carboxylic acid (silylated with 16.25 ml of N-methyl-N-trimethylsilyltrifluoroacetamide) in 50 ml of chloroform was reacted with 10 ml of trimethylsilyliodide. After stirring for 15 minutes, the mixture containing the silylated 3-iodomethyl derivative was evaporated and the residue of the 3-iodomethyl derivative was dissolved in 50 ml of acetonitrile. After 2.12 ml of tetrahydrofuran were added, the solution was stirred for 5 minutes.

An aliquot of one-thirteenth by volume of the solution was added to a solution of 295 mg of dimethylaminopyrazine in 2 ml of acetonitrile. The mixture was stirred for 3 hours and 190 μl of water were then added. The precipitate was separated by filtration and chromatographed by HPLC. There were obtained 220 mg of the purified title compound.

NMR (DMSOd$_6$) signals at 9.59 (d, 1H), 9.08 (bs, 1H), 8.82 (d, 1H), 8.71 (d, 1H), 7.23 (bs, 2H), 6.80 (s, 1H), 5.68 (q, 1H), 5.22 (q, 2H), 5.08 (d, 1H), 3.81 (s, 3H), and 3.18 (s, 6H) delta.

NMR (D$_2$O) signals at 8.60 (bs, 1H), 8.40 (s, 1H), 7.92 (bs, 1H), 6.94 (s, 1H), 5.82 (d, 1H), 5.30 (q, 2H), 5.29 (d, 1H), 3.97 (s, 3H), 3.46 (q, 2H), and 3.20 (s, 6H) delta.

EXAMPLE 5 syn-7-[2-(2-Aminothiazol-4-yl)-2-methoxyiminoacetamido]-3-[3-di-(2-hydroxyethyl)aminopyrazinium-1-ylmethyl]-3-cephem-4-carboxylate A. Preparation of syn-7-[2-(2-aminothiazol-4-yl)-2-methoxyiminoacetamido]-3-iodomethyl-3-cephem-4-carboxylic acid trimethylsilyl derivative.

N-Methyl-N-trimethylsilyltrifluoroacetamide (2.4 ml) was added to a suspension of 1.75 g of syn-7-[2-(2-aminothiazol-4-yl)-2-methoxyiminoacetamido]-3-acetoxymethyl-3-cephem-4-carboxylic acid in 8 ml of chloroform and the mixture was stirred for one hour to obtain a complete solution of the silylated derivative. The solution was treated with 1.5 ml of trimethylsilyliodide and the mixture was stirred for 15 minutes. The reaction mixture containing the silylated 3-iodomethyl derivative was evaporated to dryness, and the residue of the product was dissolved in 8 ml of dry acetonitrile and 350 μl of tetrahydrofuran were added. After the solution was stirred for 5 minutes, the solution was divided in half.

B. Preparation of title compound.

To one-half of the above solution was added a solution of 440 mg of 3-[di-(2-hydroxyethyl)amino]-pyrazine in 2 ml of dry acetonitrile containing 835 μl of bis-trimethylsilyltrifluoroacetamide and the mixture was stirred for 3 hours at room temperature. After 235 μl of water were added to the mixture, the precipitate was separated by filtration and dried. There was obtained one gram of the crude title compound which was chromatographed by HPLC to yield 250 mg of purified product.

NMR (DMSOd$_6$) signals at 9.59 (d, 1H), 9.14 (bs, 1H), 8.76, 8.63 (d,d, 2H), 7.24 (bs, 2H), 6.78 (s, 1H), 5.75 (q, 1H), 5.20 (q, 2H), 5.10 (d, 1H), 3.81 (s, 3H), and 3.78–3.00 (m, 12H) delta.

EXAMPLE 6 syn-7-[2-(2-Aminothiazol-4-yl)-2-methoxyiminoacetamido]-3-(3-diethylaminopyrazinium-1-ylmethyl)-3-cephem-4-carboxylate By following the procedures, reaction conditions and reagents employed in the preparation described by Example 2 above, except that diethylaminopyrazine is substituted for dimethylpyrazine, the title compound was obtained.

NMR (DMSOd$_6$) signals at 9.63 (d, 1H), 8.82 (d, 1H), 8.60 (bs, 1H), 7.98 (d, 1H), 6.76 (s, 1H), 5.89 (q, 1H), 5.43 (q, 2H), 5.25 (d, 1H), 3.82 (s, 3H), 3.6 (m, 6H) and 1.15 (t, 6H) delta.

EXAMPLE 7 syn-7-[2-(2-Aminothiazol-4-yl)-2-methoxyiminoacetamido]-3-(3-aminopyrazinium-1-ylmethyl)-3-cephem-4-carboxylate 3-Aminopyrazine was reacted with silylated syn-7-[2-(2-aminothiazol-4-yl)-3-iodomethyl]-3-cephem-4-carboxylic acid to provide the title compound.

NMR (DMSOd$_6$) signals at 9.56 (d, 1H), 8.65 (d, 1H), 8.55 (s, 1H), 8.44 (d, 1H), 8.03 (bs, 2H), 7.20 (bs, 2H), 6.73 (s, 1H), 5.56, 5.58 (q, d, 2H), 5.05, 4.97 (d, d, 2H), 3.29 (s, 3H), and 3.32 (q, 2H) delta.

By following the procedures and reaction conditions described in the preceding examples, the following pyrazinium and substituted pyrazinium cephalosporins represented by the formula 1 can be prepared.

| Example No. | R'$^1$ | R" | Pyrazinium |
|---|---|---|---|
| 8 | 2-AT | C$_2$H$_5$ | pyrazinium |
| 9 | 2-AT | —CH$_2$COOH | pyrazinium |
| 10 | 2-AT | —C(CH$_3$)$_2$COOH | pyrazinium |
| 11 | 2-AT | —C(CH$_3$)$_2$COOH | 3-dimethylamino-pyrazinium |
| 12 | 5-ATD | CH$_3$ | pyrazinium |
| 13 | 5-ATD | —CH$_3$COOH | pyrazinium |
| 14 | 5-ATD | —C(CH$_3$)$_2$COOH | pyrazinium |
| 15 | 2-APy | CH$_3$ | pyrazinium |
| 16 | 2-APy | C$_2$H$_5$ | pyrazinium |
| 17 | 2-APy | —CH$_2$COOH | pyrazinium |
| 18 | 2-APy | —C(CH$_3$)$_2$COOH | pyrazinium |
| 19 | 2-APy | —C(CH$_3$)$_2$COOH | 3-dimethylamino-pyrazinium |
| 20 | 2-APy | —C(CH$_3$)$_2$COOH | 3-(di-2-hydroxy-ethylamino)-pyrazinium |
| 21 | Pz | (CH$_2$)$_3$COOH | pyrazinium |
| 22 | 4-APyr | CH$_3$ | pyrazinium |
| 23 | 2-APyr | CH$_3$ | pyrazinium |
| 24 | 2-APyr | —C(CH$_3$)$_2$COOH | 3-methyl-pyrazinium |
| 25 | 4-APyr | —C(CH$_3$)$_2$COOH | 3-(n-propyl)-pyrazinium |
| 26 | 3-APz | CH$_3$ | pyrazinium |
| 27 | 3-APz | n-C$_3$H$_7$ | pyrazinium |
| 28 | 3-APz | —CH$_2$COOH | pyrazinium |
| 29 | 3-APz | —(CH$_3$)$_2$COOH | pyrazinium |
| 30 | 3-APz | —(CH$_3$)$_2$COOH | 3-diethylamino-pyrazinium |

$^1$AT = 2-aminothiazol-4-yl;
ATD = 5-aminothiadiazol-4-yl;
APy = aminopyridine-6-yl;
APyr = aminopyrimidine;
APz = aminopyrazole-5-yl;
Pz = pyrazol-5-yl.

I claim:
1. A compound of the formula

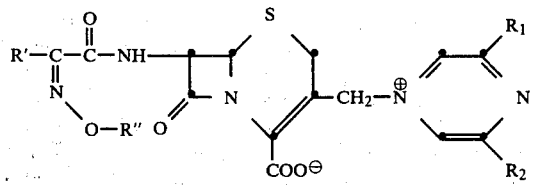

wherein R' is a 5-membered heterocyclic ring of the formulas

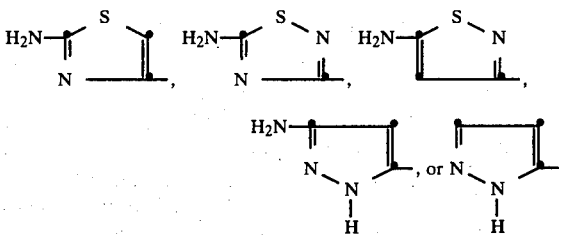

or a 6-membered heterocyclic ring of the formulas

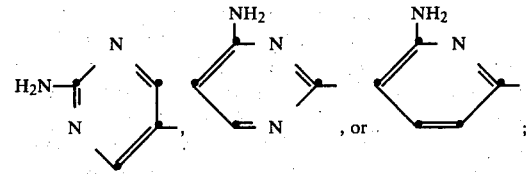

R" is hydrogen, C$_1$–C$_4$ alkyl, a carboxy-substituted alkyl or carboxy-substituted cycloalkyl group of the formula

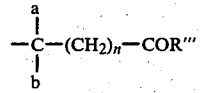

wherein a and b independently are hydrogen or C$_1$–C$_3$ alkyl, and a and b when taken together with the carbon atom to which they are attached form a C$_3$–C$_7$-membered carbocyclic ring, n is 0–3, and R''' is hydroxy, $C_1$–$C_4$ alkoxy, or amino; or R'' is a carbamoyl group of the formula

wherein R'''' is hydrogen, $C_1$–$C_4$ alkyl, phenyl, or phenyl substituted $C_1$–$C_3$ alkyl; $R_1$ is amino, $C_1$–$C_4$ alkylamino, di($C_1$–$C_4$ alkyl)amino, $C_1$–$C_4$ hydroxyalkylamino, or di($C_1$–$C_4$ hydroxyalkyl)amino; $R_2$ *is hydrogen or $C_1$–$C_4$ alkyl*; and the pharmaceutically acceptable non-toxic salts thereof.

2. The compound of claim 1 wherein R'' is hydrogen.

3. The compound of claim 1 wherein R'' is a group of the formula

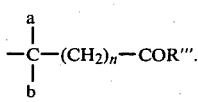

4. The compound of claim 3 wherein R''' is hydroxy and a and b are hydrogen or methyl.

5. The compound of claim 1 wherein R'' is $C_1$–$C_4$ alkyl.

6. The compound of claim 5 wherein R'' is methyl.

7. The compound of claim 6 wherein R' is

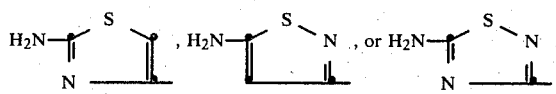

8. The compound of claim 6 wherein $R_1$ is $C_1$–$C_4$ alkylamino, di($C_1$–$C_4$ alkyl)amino, $C_2$–$C_4$ hydroxyalkylamino, or di($C_2$–$C_4$ hydroxyalkyl)amino, and $R_2$ is hydrogen.

9. The compound of claim 8 wherein $R_1$ is di($C_1$–$C_4$ alkyl)amino or $C_1$–$C_4$ alkylamino.

10. The compound of claim 9, said compound being syn-7-[2-(2-aminothiazol-4-yl)-2-methoxyiminoacetamido]-3-(3-dimethylaminopyrazinium-1-ylmethyl)-3-cephem-4-carboxylate.

11. The compound of claim 6 wherein $R_1$ is $C_2$–$C_4$ hydroxyalkylamino or di($C_2$–$C_4$ hydroxyalkyl)amino and $R_2$ is hydrogen.

12. The compound of claim 11, said compound being syn-7-[2-(2-aminothiazol-4-yl)-2-methoxyiminoacetamido]-3-[3-di-(2-hydroxyethyl)aminopyrazinium-1-ylmethyl]-3-cephem-4-carboxylate.

13. The antibiotic formulation comprising a therapeutically effective amount of a compound of claim 1 and a pharmaceutically acceptable diluent.

14. The antibiotic formulation of claim 13 wherein R' is 2-aminothiazol-4-yl and R''' is methyl.

15. The formulation of claim 13 wherein $R_1$ is diethylamino and $R_2$ is hydrogen.

16. The method for treating bacterial infections in a mammal which comprises administering to said mammal in a dose of between about 100 mg. and about 2 g. of a compound of claim 1.

17. The method of claim 16 wherein R' is 2-aminothiazol-4-yl and R'' is methyl.

18. The method of claim 16 wherein $R_1$ is dimethylamino and $R_2$ is hydrogen.

19. A compound of the formula wherein R is formyl; $R_1$ is amino, $C_1$–$C_4$ alkylamino, di($C_1$–$C_4$ alkyl)amino, $C_1$–$C_4$ hydroxyalkylamino, or di($C_1$–$C_4$ hydroxyalkyl)amino; and $R_2$ is hydrogen or $C_1$–$C_4$ alkyl; and the acid addition salts thereof.

* * * * *